(12) United States Patent
Lovell et al.

(10) Patent No.: US 9,771,398 B2
(45) Date of Patent: *Sep. 26, 2017

(54) METHOD OF PROTEIN EXTRACTION FROM CELLS

(71) Applicants: Arbor Vita Corporation, Sunnyvale, CA (US); Becton, Dickinson and Company, Franklin Lakes, NJ (US)

(72) Inventors: Stephen Lovell, Sparks, MD (US); Lydia Blank, Sparks (MD); Virginia Crews, Sparks, MD (US); Nancy Hasse, Sparks, MD (US); Peter Lu, Sunnyvale, CA (US); Johannes Schweizer, Sunnyvale, CA (US); John Mantlo, Westminster, MD (US)

(73) Assignees: Arbor Vita Corporation, Sunnyvale, CA (US); Becton, Dickinson and Company, Franklin Lakes, NJ (US)

( * ) Notice: Subject to any disclaimer, the term of this patent is extended or adjusted under 35 U.S.C. 154(b) by 75 days.

This patent is subject to a terminal disclaimer.

(21) Appl. No.: 14/598,148

(22) Filed: Jan. 15, 2015

(65) Prior Publication Data

US 2015/0266928 A1  Sep. 24, 2015

Related U.S. Application Data

(63) Continuation of application No. 11/747,830, filed on May 11, 2007, now Pat. No. 8,962,262.

(60) Provisional application No. 60/747,076, filed on May 11, 2006.

(51) Int. Cl.
*C07K 14/005* (2006.01)
*C07K 14/82* (2006.01)
*G01N 33/569* (2006.01)
*C07K 1/14* (2006.01)
*C12N 7/00* (2006.01)

(52) U.S. Cl.
CPC ............ *C07K 14/005* (2013.01); *C07K 1/145* (2013.01); *C07K 14/82* (2013.01); *C12N 7/00* (2013.01); *G01N 33/56983* (2013.01); *C12N 2710/20051* (2013.01); *G01N 2333/025* (2013.01)

(58) Field of Classification Search
None
See application file for complete search history.

(56) References Cited

U.S. PATENT DOCUMENTS

| 3,303,038 A | 2/1967 | Klevens |
| 3,546,334 A | 12/1970 | Lerner et al. |
| 3,862,112 A * | 1/1975 | Ishida ............... A23J 1/008 426/431 |
| 4,578,282 A | 3/1986 | Harrison |
| 4,649,192 A | 3/1987 | Van Wijnendaele et al. |
| 4,857,300 A | 8/1989 | Maksem |
| 5,104,640 A | 4/1992 | Stokes |
| 5,132,205 A | 7/1992 | Pronovost et al. |
| 5,196,182 A | 3/1993 | Ryan |
| 5,256,571 A | 10/1993 | Hurley et al. |
| 5,432,056 A | 7/1995 | Hartman et al. |
| 5,620,869 A | 4/1997 | Woodard et al. |
| 5,773,277 A | 6/1998 | Hashimoto et al. |
| 6,004,771 A | 12/1999 | Thornton |
| 6,245,568 B1 * | 6/2001 | Volkin ............... A61K 39/12 424/204.1 |
| 6,337,189 B1 * | 1/2002 | Ryan ............... G01N 1/30 435/40.5 |
| 6,488,671 B1 | 12/2002 | Constantz et al. |
| 6,890,729 B2 | 5/2005 | Mielzynska et al. |
| 7,115,719 B2 | 10/2006 | Paulsen |
| 7,306,926 B2 | 12/2007 | Doeberitz et al. |
| 8,962,262 B2 | 2/2015 | Lovell et al. |
| 9,207,240 B2 | 12/2015 | Malick et al. |
| 2003/0175852 A1 | 9/2003 | Kalra et al. |
| 2004/0018487 A1 | 1/2004 | Lu et al. |
| 2004/0101947 A1 | 5/2004 | Engel et al. |
| 2004/0180388 A1 | 9/2004 | Von Knebel et al. |
| 2005/0019841 A1 | 1/2005 | Garman et al. |
| 2005/0032105 A1 | 2/2005 | Bair et al. |
| 2005/0037969 A1 | 2/2005 | Lu et al. |
| 2005/0112552 A1 | 5/2005 | Herrero et al. |
| 2005/0142541 A1 | 6/2005 | Lu et al. |
| 2006/0148711 A1 | 7/2006 | Lu et al. |
| 2007/0212682 A1 | 9/2007 | Yu et al. |
| 2007/0292899 A1 | 12/2007 | Lovell et al. |
| 2009/0123910 A1 | 5/2009 | Malick et al. |
| 2016/0216258 A1 | 7/2016 | Malick et al. |

FOREIGN PATENT DOCUMENTS

| EP | 0174106 A2 | 3/1986 |
| EP | 0174106 A3 | 3/1986 |

(Continued)

OTHER PUBLICATIONS

Notice of allowance dated Aug. 18, 2015 for U.S. Appl. No. 11/985,547.

(Continued)

*Primary Examiner* — Agnieszka Boesen
(74) *Attorney, Agent, or Firm* — Wilson Sonsini Goodrich & Rosati

(57) ABSTRACT

Methods for producing a protein extract from cells, such as cells containing viral proteins, are provided. In general terms, the methods involve: increasing the pH of the cells to a pH of at least about pH 10.0 to produce an intermediate composition, and then, in the presence of a non-ionic detergent, neutralizing the pH of the intermediate composition to produce the protein extract. Kits and compositions for practicing the subject methods are also provided.

26 Claims, No Drawings

(56) References Cited

FOREIGN PATENT DOCUMENTS

| EP | 0 363 110 A2 | 4/1990 |
|---|---|---|
| EP | 0363 108 A2 | 4/1990 |
| EP | 0382519 A2 | 8/1990 |
| EP | 0 363 110 A3 | 7/1991 |
| EP | 0363 108 A3 | 7/1991 |
| EP | 0363110 B1 | 9/1995 |
| JP | H03-43094 A | 2/1991 |
| JP | 2004534831 A | 11/2004 |
| JP | 2005-538360 | 12/2005 |
| WO | WO 00/57906 A1 | 10/2000 |
| WO | WO-03000877 A2 | 1/2003 |
| WO | WO 2005/088311 A1 | 9/2005 |
| WO | WO 2007/134252 A1 | 11/2007 |

OTHER PUBLICATIONS

Ausubel, et al. Current Protocols in Molecular Biology, vol. 1, Wiley & Sons, 1995.
Baker. Principles of Biological Microtechnique: A Study of Fixation and Dyeing, 1959.
Bird, et al. Single-chain antigen-binding proteins. Science. Oct. 21, 1988;242(4877):423-6.
Bosch, et al. The Aetiology of Cervical Cancer. NHS Cancer Screening Programmes. 2005.
Demay. Common Problem in Papanicolaou Smear Interpretation. Arch. Pathol. Lab. Med. 1997; 121:229-238.
Elshal, et al. Multiplex bead array assays: performance evaluation and comparison of sensitivity to ELISA. Methods. Apr. 2006;38(4):317-23.
Elston, et al. The identification of a conserved binding motif within human papillomavirus type 16 E6 binding peptides, E6AP and E6BP. J Gen Virol. Feb. 1998;79 ( Pt 2):371-4.
European office action dated Mar. 29, 2012 for EP Application No. 07797439.2.
European office action dated Mar. 29, 2012 for EP Application No. 08850323.0.
European office action dated Sep. 6, 2012 for EP Application No. 08850323.0.
European office action dated Sep. 10, 2012 for EP Application No. 07797439.2.
European office action dated Sep. 10, 2012 for EP Application No. 08850323.0.
European search report and search opinion dated Dec. 2, 2010 for Application No. 07797439.2.
European search report dated Dec. 3, 2010 for Application No. 08850323.
Gu, et al. Proteomic analysis of high-grade dysplastic cervical cells obtained from ThinPrep slides using laser capture microdissection and mass spectrometry. J Proteome Res. Nov. 2007;6(11):4256-68.
Harlow, et al. Antibodies: A Laboratory Manual Cold Spring Harbor Laboratory. Cold Spring Harbor. N.Y. 1988.
Hatefi, et al. Solubilization of particulate proteins and nonelectrolytes by chaotropic agents. Proc. Natl. Acad. Sci. 1962; 62:1129-1136.
Hood, et al. Immunology, 2nd edition, 1984.
Hunkapiller, et al. The growing immunoglobulin gene superfamily. Nature. Sep. 4-10, 1986;323(6083):15-6.
Huston, et al. Protein engineering of antibody binding sites: recovery of specific activity in an anti-digoxin single-chain Fv analogue produced in *Escherichia coli*. Proc Natl Acad Sci U S A. Aug. 1988;85(16):5879-83.
International search report dated Jan. 27, 2009 for PCT Application No. US2008/83707.
International search report dated Oct. 29, 2007 for PCT Application No. US2007/68809.
Koss. The Papanicolaou Test for Cervical Cancer Detection: A Triumph and a Tragedy. JAMA. 1989; 261: 737-743.
Lanzavecchia, et al. The use of hybrid hybridomas to target human cytotoxic T lymphocytes. Eur J Immunol Jan. 1987;17(1):105-11.
Notice of allowance dated Jan. 29, 2015for U.S. Appl. No. 11/747,830.
Notice of allowance dated Oct. 24, 2014 for U.S. Appl. No. 11/747,830.
Notice of allowance dated Dec. 8, 2014for U.S. Appl. No. 11/747,830.
Office action dated Feb. 1, 2011 for U.S. Appl. No. 11/747,830.
Office action dated Feb. 14, 2011 for U.S. Appl. No. 11/985,547.
Office action dated Feb. 29, 2012 for U.S. Appl. No. 11/985,547.
Office action dated Mar. 21, 2014 for U.S. Appl. No. 11/747,830.
Office action dated May 16, 2013 for U.S. Appl. No. 11/985,547.
Office action dated Jun. 10, 2010 for U.S. Appl. No. 11/747,830.
Office action dated Jun. 19, 2012 for U.S. Appl. No. 11/985,547.
Office action dated Sep. 30, 2009 for U.S. Appl. No. 11/747,830.
Office action dated Oct. 11, 2012 for U.S. Appl. No. 11/747,830.
Office action dated Oct. 13, 2011 for U.S. Appl. No. 11/747,830.
Office action dated Nov. 20, 2014 for U.S. Appl. No. 11/985,547.
Office action dated Aug. 23, 2013 for U.S. Appl. No. 11/747,830.
O'Neil, et al. Eds. Polyoxyethyene Alcohols. No. 7659. The Merck Index. 13$^{th}$ Edition. Merck Research Laboratories. 2001. 7663.
Principles and standard conditions for purification techniques. Protein purification Handbook. Amersham Pharmacia Biotech. 1999; 71-95.
Protein purification handbook. Amersham Pharmacia Biotech, p. 71, 1999.
Romeo, et al. Infrared micro-spectroscopic studies of epithelial cells. Biochim Biophys Acta. Jul. 2006;1758(7):915-22.
Schneider, et al. Mutagenesis and selection of PDZ domains that bind new protein targets. Nat. Biotech. 1999;17:170-175.
Umbreit, et al. Relation of detergent HLB number to solubilization and stabilization of D-alanine carboxypeptidase from Bacillus subtillis membreanes. Proc. Natl. Acad. Sci. USA. 1973; 70: 2997.
Veerisetty, et al. Purification of Some Legume Carlaviruses. Phytopathology. 1977; 68:59-64.
Vignali. Multiplexed particle-based flow cytometric assays. J Immunol Methods. 2000; 243(1-2):243-55.
Williams, et al. Tissue Preparation for Immunocytochemisty. J Clin. Pathol. 1997; 50:422-428.
Yan. The Characteristic and Application of Nonionic Surfactant (in Chinese with English abstract). Guizhou Chemical Industry. Oct. 2005; 30(5):4-7 and 22.
Office action dated Oct. 14, 2015 for CA Application No. 2,705,765.
Office action dated Dec. 2, 2016 for U.S. Appl. No. 14/932,693.

\* cited by examiner

SEQUENCE LISTING

<160> NUMBER OF SEQ ID NOS: 1

<210> SEQ ID NO 1
<211> LENGTH: 103
<212> TYPE: PRT
<213> ORGANISM: Homo sapiens

<400> SEQUENCE: 1

```
Pro Ser Glu Leu Lys Gly Lys Phe Ile His Thr Lys Leu Arg Lys Ser
1               5                   10                  15

Ser Arg Gly Phe Gly Phe Thr Val Val Gly Gly Asp Glu Pro Asp Glu
            20                  25                  30

Phe Leu Gln Ile Lys Ser Leu Val Leu Asp Gly Pro Ala Ala Leu Asp
        35                  40                  45

Gly Lys Met Glu Thr Gly Asp Val Ile Val Ser Val Asn Asp Thr Cys
    50                  55                  60

Val Leu Gly His Thr His Ala Gln Trp Lys Ile Phe Gln Ser Ile Pro
65                  70                  75                  80

Ile Gly Ala Ser Val Asp Leu Glu Leu Cys Arg Gly Tyr Pro Leu Pro
                85                  90                  95

Phe Asp Pro Asp Asp Pro Asn
            100
```

METHOD OF PROTEIN EXTRACTION FROM CELLS

CROSS-REFERENCE

This application is a continuation application of U.S. patent application Ser. No. 11/747,830 filed May 11, 2007, which claims the benefit of U.S. Provisional Application No. 60/747,076 filed May 11, 2006. The disclosures of these applications are hereby incorporated by reference, as if set forth in this document, for all purposes.

SEQUENCE LISTING

The instant application contains a Sequence Listing which has been submitted electronically in ASCII format and is hereby incorporated by reference in its entirety. Said ASCII copy, created on May 30, 2014, is named 34170_704_301_SL.txt and is 1,320 bytes in size.

BACKGROUND OF THE INVENTION

In particular, the instant methods may be employed to detect the E6 protein from oncogenic strains of HPV. In these embodiments, the capture agent employed in the detection method may be, for example, an antibody or a polypeptide comprising a PDZ domain that binds to a PDZ ligand (i.e., a binding site for a PDZ domain) contained in the E6 protein. For example, the instant E6 detection binding method may employ a PDZ domain-containing protein that contains the second PDZ of MAGI-1, or the PDZ domain of DLG or TIP1, etc, as described in published application US 20040018487 (published on Jan. 29, 2004) and incorporated herein by reference in its entirety. Exemplary PDZ domain-containing proteins and PDZ domain sequences are shown in TABLE 2 and EXAMPLE 4 of application US 20040018487. The term "PDZ domain" also encompasses variants (e.g., naturally occurring variants) of the sequences (e.g., polymorphic variants, variants with conservative substitutions, and the like) and domains from alternative species (e.g. mouse, rat). Typically, PDZ domains are substantially identical to those shown in U.S. patent application Ser. No. 09/724,553 which is herein incorporated by reference, e.g., at least about 70%, at least about 80%, or at least about 90% amino acid residue identity when compared and aligned for maximum correspondence. It is appreciated in the art that PDZ domains can be mutated to give amino acid changes that can strengthen or weaken binding and to alter specificity, yet they remain PDZ domains (Schneider et al, 1998, Nat. Biotech. 17:170-5). Unless otherwise indicated, a reference to a particular PDZ domain (e.g. a MAGI-1 domain 2) is intended to encompass the particular PDZ domain and HPV E6-binding variants thereof. In other words, if a reference is made to a particular PDZ domain, a reference is also made to variants of that PDZ domain that bind oncogenic E6 protein of HPV, as described below. In this respect it is noted that the numbering of PDZ domains in a protein may change. For example, the MAGI-1 domain 2 (of amino acid sequence PSELKGKFIHTKLRKSSRGFGFTVVGGDEPDEFLQIKSLVLDGPAALD GKMETGDVI VSVNDTCVLGHTHAQWKIFQSIPIGASVDLELCRGYPLPFDPDDPN) (SEQ ID NO: 1), as referenced herein, may be referenced as MAGI-1 domain 1 in other literature. As such, when a particular PDZ domain of a protein is referenced in this application, this reference should be understood in view of the sequence of that domain, as described herein, particularly in the sequence listing Table 2 of Application US 20040018487, shows the relationship between the sequences of the sequence listing and the names and Genbank accession numbers for various domains, where appropriate. As used herein, the term "PDZ protein" refers to a naturally occurring protein containing a PDZ domain. Exemplary PDZ proteins include CASK, MPP1, DLG1, DLG2, PSD95, NeDLG, TIP-33, SYN1a, TIP-43, LDP, LIM, LIMK1, LIMK2, MPP2, NOS1, AF6, PTN-4, prIL16, 41.8 kD, KIAA0559, RGS12, KIAA0316, DVL1, TIP-40, TIAM1, MINT1, MAGI-1, MAGI-2, MAGI-3, KIAA0303, CBP, MINT3, TIP-2, KIAA0561, and TIP-1. As used herein, the term "PDZ-domain polypeptide" refers to a polypeptide containing a PDZ domain, such as a fusion protein including a PDZ domain sequence, a naturally occurring PDZ protein, or an isolated PDZ domain peptide. A PDZ-domain polypeptide may therefore be about 60 amino acids or more in length, about 70 amino acids or more in length, about 80 amino acids or more in length, about 90 amino acids or more in length, about 100 amino acids or more in length, about 200 amino acids or more in length, about 300 amino acids or more in length, about 500 amino acids or more in length, about 800 amino acids or more in length, about 1000 amino acids or more in length, usually up to about 2000 amino acids or more in length, about 50-2000 amino acids in length, about 50-1500 amino acids in length, about 50-1000 amino acids in length, about 60-1000 amino acids in length, about 70-1000 amino acids in length. PDZ domain peptides are usually no more than about 200 amino acids (e.g. 50-200 amino acids, 60-180 amino acids, 80-120 amino acids, or 90-110 amino acids), and encode a PDZ domain.

Despite the success of such cytological tests, the tests are prone to error. For example, it has been estimated that up to 40% of conventional Pap tests are compromised by the presence of contaminants such as mucous, blood cells and obscuring inflammatory cells. These contaminants lead to false negative results, false positive results, and a significant amount of follow-up work. See, e.g., Koss, L. G. (1989), The Papanicolaou Test for Cervical Cancer Detection: A Triumph and a Tragedy, JAMA 261:737-743; see also DeMay, "Problems in Pap Smear Interpretation", Arch. Pathol. Lab. Med. 121:229-23 (1997).

In view of the above, there is a need for complementary molecular diagnostic methods for the analysis of cells that are present in a liquid medium containing a fixative. Such methods are not straightforward, however, because it is not always possible to perform such methods on fixed cells. For example, certain fixatives (e.g., those transport media employed in THINPREP™ or SUREPATH™ test systems) may cause particular cellular proteins to precipitate or aggregate, thereby making those proteins insoluble and difficult or impossible to reliably detect using conventional means, e.g., using an enzyme-linked immunosorbancy assay (ELISA) or another immunological test.

There is therefore a great need for methods and compositions for extracting proteins from fixed cells in a manner that allows them to be suitable for use in molecular, e.g., immunological, detection assays. The invention described herein meets this need, and others.

LITERATURE

Literature of interest includes: U.S. Pat. Nos. 6,890,729, 6,337,189 and published U.S. patent application 20050032105.

SUMMARY OF THE INVENTION

Methods for producing a protein extract from cells, preferably fixed cells, are provided. In general terms, the methods involve: increasing the pH of the cells to a pH of at least about pH 10.0 to produce an intermediate composition, and then, in the presence of a non-ionic detergent, neutralizing the pH of the intermediate composition to produce the protein extract. The method may include: a) contacting the cells with an extraction reagent to produce an intermediate composition having a pH of at least about pH 10.0; and b) contacting the intermediate composition with a neutralizing reagent to neutralize the pH of the intermediate composition and produce the protein extract. One or both of the extraction reagent and the neutralization reagent contains the non-ionic detergent. In certain embodiments, the fixed cells may be fixed exfoliated cervical cells.

Definitions

Unless defined otherwise, all technical and scientific terms used herein have the same meaning as commonly understood by one of ordinary skill in the art to which this invention belongs. Still, certain elements are defined below for the sake of clarity and ease of reference.

The term "cellular sample" as used herein relates to a liquid composition containing one or more cells of interest. A cellular sample may be a clinical sample containing cells removed from (e.g., dissected or exfoliated from) an individual, including but not limited to, for example, cells from plasma, serum, spinal fluid, semen, lymph fluid, the external sections of the skin, respiratory, intestinal, and genitourinary tracts, tears, saliva, milk, blood cells, tumors, or organs. In other embodiments, the cellular sample may contains cells grown in vitro (including but not limited to cells in cell culture medium, virally infected cells, recombinant cells, etc.). In certain embodiments, the cellular sample may contain cells that are at most risk of being infected by HPV. In these embodiments, the cells may be obtained from a cervix, vulva, vagina, anus, penis, mouth or throat. In certain embodiments, the cells are from mucous membrane and may be epithelial in origin. A cellular sample may or may not contain contaminants other than exfoliated or dissected cells. For example, mucous, or bacterial, yeast or blood cells may be present in a cellular sample.

"HPV" is human Papillomavirus, including but not limited to HPV strain 4, 11, 20, 24, 28, 36, 48, 50, 16, 18, 31, 35, 30, 39, 45, 51, 52, 56, 59, 58, 33, 66, 68, 69, 26, 53, 73, and 82.

An "oncogenic HPV strain" is an HPV strain that is known to cause cervical cancer as determined by the National Cancer Institute (NCI, 2001).

An "oncogenic E6 protein" is an E6 protein encoded by an oncogenic HPV strain. Exemplary oncogenic strains are: HPV 26, HPV 53, HPV 66, HPV 73, HPV 82, HPV 16, HPV 18, HPV 31, HPV 35, HPV 30, HPV 39, HPV 45, HPV 51, HPV 52, HPV 56, HPV 59, HPV 58, HPV 33, HPV 66, HPV 68, HPV 69, and HPV 82. The amino acid sequences of oncogenic E6 proteins are deposited in NCBI's GenBank database. While not wishing to be bound to the theory, it is generally believed that HPV strain 4, 11, 20, 24, 28, 36, 48, and 50 are not oncogenic.

The terms "polypeptide" and "protein" are used interchangeably. The term "polypeptide" includes polypeptides in which the conventional backbone has been replaced with non-naturally occurring or synthetic backbones, and peptides in which one or more of the conventional amino acids have been replaced with one or more non-naturally occurring or synthetic amino acids.

The term "fusion protein" or grammatical equivalents thereof references a protein composed of a plurality of polypeptide components, that while not attached in their native state, are joined by their respective amino and carboxyl termini through a peptide linkage to form a single continuous polypeptide. Fusion proteins may be a combination of two, three or even four or more different proteins. The term polypeptide includes fusion proteins, including, but not limited to, fusion proteins with a heterologous amino acid sequence, fusions with heterologous and homologous leader sequences, with or without N-terminal methionine residues; immunologically tagged proteins; fusion proteins with detectable fusion partners, e.g., fusion proteins including as a fusion partner a fluorescent protein, β-galactosidase, luciferase, and the like.

In general, polypeptides may be of any length, e.g., greater than 2 amino acids, greater than 4 amino acids, greater than about 10 amino acids, greater than about 20 amino acids, greater than about 50 amino acids, greater than about 100 amino acids, greater than about 300 amino acids, usually up to about 500 or 1000 or more amino acids. "Peptides" are generally greater than 2 amino acids, greater than 4 amino acids, greater than about 10 amino acids, greater than about 20 amino acids, usually up to about 50 amino acids. In some embodiments, peptides are between 5 and 30 amino acids in length. Polypeptides may be natural in that that they may be encoded by the genome of an organism or virus, or un-natural in that they are non-naturally occurring.

The term "capture agent" refers to an agent that binds a protein through an interaction that is sufficient to permit the agent to bind and concentrate the protein from a homogeneous mixture of different proteins. Accordingly, the term "capture agent" refers to a molecule or a multi-molecular complex which can specifically bind an analyte, e.g., specifically bind an analyte for the capture agent, with a dissociation constant ($K_D$) of less than about $10^{-6}$ M without binding to other targets. The binding interaction may be mediated by an affinity region of the capture agent. Representative capture agents include antibodies (including fragments and mimetics thereof) and PDZ domain-containing proteins, etc.

The term "specific binding" refers to the ability of a capture agent to preferentially bind to a particular protein that is present in a homogeneous mixture of different proteins. In certain embodiments, a specific binding interaction will discriminate between a particular protein and other proteins in a sample, in some embodiments more than about 10 to 100-fold or more (e.g., more than about 1000- or 10,000-fold).

The term "capture agent/protein complex" is a complex that results from the specific binding of a capture agent with a protein, i.e., a "binding partner pair". A capture agent and a protein for the capture agent specifically bind to each other under "conditions suitable for specific binding", where such conditions are those conditions (in terms of salt concentration, pH, detergent, protein concentration, temperature, etc.) which allow for binding to occur between capture agents and proteins to bind in solution. Such conditions, particularly with respect to antibodies and their antigens, are well known in the art (see, e.g., Harlow and Lane (Antibodies: A Laboratory Manual Cold Spring Harbor Laboratory, Cold Spring Harbor, N.Y. (1989)). In certain embodiments, the affinity between a capture agent and protein that are specifically bound in a capture agent/protein complex is characterized by a $K_D$ (dissociation constant) of less than $10^{-6}$ M, less than $10^{-7}$ M, less than $10^{-8}$ M, less than $10^{-9}$ M, or less than about $10^{-10}$ M.

"Binding partners" and equivalents refer to pairs of molecules that can be found in a capture agent/analyte complex, i.e., exhibit specific binding with each other.

The terms "antibody" and "immunoglobulin" are used interchangeably herein to refer to a capture agent that has at least an epitope binding domain of an antibody. These terms are well understood by those in the field, and refer to a protein containing one or more polypeptides that specifically binds an antigen. One form of antibody constitutes the basic structural unit of an antibody. This form is a tetramer and consists of two identical pairs of antibody chains, each pair having one light and one heavy chain. In each pair, the light and heavy chain variable regions are together responsible for binding to an antigen, and the constant regions are responsible for the antibody effector functions.

The recognized immunoglobulin polypeptides include the kappa and lambda light chains and the alpha, gamma ($IgG_1$, $IgG_2$, $IgG_3$, $IgG_4$), delta, epsilon and mu heavy chains or equivalents in other species. Full-length immunoglobulin "light chains" (of about 25 kDa or about 214 amino acids) comprise a variable region of about 110 amino acids at the $NH_2$-terminus and a kappa or lambda constant region at the COOH-terminus. Full-length immunoglobulin "heavy chains" (of about 50 kDa or about 446 amino acids), similarly comprise a variable region (of about 116 amino acids) and one of the aforementioned heavy chain constant regions, e.g., gamma (of about 330 amino acids).

The terms "antibodies" and "immunoglobulin" include antibodies or immunoglobulins of any isotype, fragments of antibodies which retain specific binding to antigen, including, but not limited to, Fab, Fv, scFv, and Fd fragments, chimeric antibodies, humanized antibodies, single-chain antibodies, and fusion proteins comprising an antigen-binding portion of an antibody and a non-antibody protein. The antibodies may be detectably labeled, e.g., with a radioisotope, an enzyme which generates a detectable product, a fluorescent protein, and the like. The antibodies may be further conjugated to other moieties, such as members of specific binding pairs, e.g., biotin (member of biotin-avidin specific binding pair), and the like. The antibodies may also be bound to a solid support, including, but not limited to, polystyrene plates or beads, and the like. Also encompassed by the terms are Fab', Fv, F(ab')$_2$, and or other antibody fragments that retain specific binding to antigen.

Antibodies may exist in a variety of other forms including, for example, Fv, Fab, and (Fab')$_2$, as well as bi-functional (i.e. bi-specific) hybrid antibodies (e.g., Lanzavecchia et al., Eur. J. Immunol. 17, 105 (1987)) and in single chains (e.g., Huston et al., Proc. Natl. Acad. Sci. U.S.A., 85, 5879-5883 (1988) and Bird et al., Science, 242, 423-426 (1988), which are incorporated herein by reference). (See, generally, Hood et al, "Immunology", Benjamin, N.Y., 2nd ed. (1984), and Hunkapiller and Hood, Nature, 323, 15-16 (1986)). Monoclonal antibodies and "phage display" antibodies are well known in the art and encompassed by the term "antibodies".

The term "assessing" includes any form of measurement, and includes determining if an element is present or not. The terms "determining", "measuring", "evaluating", "assessing" and "assaying" are used interchangeably and may include quantitative and/or qualitative determinations. Assessing may be relative or absolute. "Assessing the presence of" includes determining the amount of something present, and/or determining whether it is present or absent.

By "remote location" is meant a location other than the location at which cells are obtained and deposited into a fixative-containing liquid. For example, a remote location could be a different room in the same building in which cells are obtained (e.g., another laboratory), a different building in the same building complex as the cells are obtained, or a different location in the same city, state or country, etc. When a cellular sample is indicated as being "received" from a remote location, the cellular sample may be obtained from the remote location or hand-delivered, mailed or couriered from the remote location, for example.

"Communicating" information refers to any means of getting that information from one location to the next, whether by physically transporting printed material or computer readable media containing the information (e.g., by mail), or by transmitting the information. If information is transmitted, a digital or analog signal representing the information (e.g., a electromagnetic signal such as a light or electrical signal) is transmitted over a suitable communication channel (for example, a private, public or wireless network). Any convenient means may be employed for transmitting the data, e.g., facsimile, modem, internet, e-mail, etc.

As used herein, the term "transport medium" is used to describe liquid suitable for collection of cells and the preservation of those cells in a manner that allows them to be suitable for liquid-based cytological studies. Transport media are commonly employed in Pap test. Cells deposited into transport medium may or may not be transported from one location to another in that medium. Transport media contain fixative. Deposition of cells into a transport medium fixes the cells to produce fixed cells. Representative transport media include SUREPATH™ or PRESERVCYT™ transport media.

A "fixed cell" is a cell that has been treated with and cytologically preserved by a chemical fixative. Fixed cells are usually suitable for staining and subsequent morphological and/or cytological analysis by light microscopy.

INCORPORATION BY REFERENCE

All publications and patent applications mentioned in this specification are herein incorporated by reference to the same extent as if each individual publication or patent application was specifically and individually indicated to be incorporated by reference.

DETAILED DESCRIPTION OF THE INVENTION

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

Methods for producing a protein extract from fixed cells are provided. In general terms, the methods involve: increasing the pH of the fixed cells to a pH of at least about pH 10.0 to produce an intermediate composition, and then, in the presence of a non-ionic detergent, neutralizing the pH of the intermediate composition to produce the protein extract. The method may include: a) contacting the fixed cells with an extraction reagent to produce an intermediate composition having a pH of at least about pH 10.0; and b) contacting the intermediate composition with a neutralizing reagent to neutralize the pH of the intermediate composition and produce the protein extract. One or both of the extraction reagent and the neutralization reagent contains the non-ionic detergent. In certain embodiments, the fixed cells may be fixed exfoliated cervical cells. Kits and compositions for practicing the subject methods are also provided. The subject methods find use in a variety of different applications, including diagnostic tests that detect particular proteins in the resultant protein extract.

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, the singular forms "a," "an" and "the" include plural reference unless the context clearly dictates otherwise.

Where a range of values is provided, it is understood that each intervening value, to the tenth of the unit of the lower limit unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also'included in the invention.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing and disclosing components that are described in the publications which might be used in connection with the presently described invention.

As summarized above, the subject invention provides methods and compositions for producing a protein extract from fixed cells. In describing the invention in greater detail, the methods are described first followed by a description of the kits and systems for use in practicing the subject methods.

Methods of Protein Extraction

As noted above, the invention provides a method for producing a protein extract from fixed cells. In general, the methods involve two steps: a) contacting the fixed cells with an extraction reagent having a pH that is greater than about pH. 10.0 to produce an intermediate composition and b) contacting the intermediate composition with a neutralizing reagent. The extraction reagent and/or the neutralizing reagent contains a non-ionic detergent. The resultant protein extract contains a non-ionic detergent and has a pH that is neutral (i.e., between about pH 7.0 and about pH 8.0). The methods generally produce a protein extract containing proteins that are readily detectable using capture agents for those proteins. As such, a protein extract produced by the instant methods are generally suitable for use in binding assays, e.g., immunological assays, for detection of those proteins.

In certain embodiments the methods may include: increasing the pH of the fixed cells to a pH of at least about pH 10.0 to produce an intermediate composition, and then, in the presence of a non-ionic detergent, neutralizing the pH of the intermediate composition to produce the protein extract. Since, as mentioned above, the non-ionic detergent may be present in either the extraction reagent or the neutralizing reagent (or in both the extraction reagent and the neutralizing reagent), certain embodiments of the instant methods include: a) contacting fixed cells with an extraction reagent to produce an intermediate composition having a pH of at least about pH 10.0; and b) contacting the intermediate composition with a neutralizing reagent comprising a non-ionic detergent; to neutralize said pH of the intermediate composition and produce the protein extract. In other embodiments, the method may include: a) contacting the fixed cells with an extraction reagent comprising a non-ionic detergent to produce an intermediate composition having a pH of at least about pH 10.0; and, b) contacting the intermediate composition with a neutralizing reagent; to neutralize the pH of the intermediate composition and produce the protein extract.

In certain embodiments, the protein extract produced by the instant methods may contain more protein that is accessible to capture agents than a protein extract made using other methods, e.g., methods that do not employ: a high pH extraction step (i.e., a step that increases pH to greater than about pH 10.0 or pH 11.0), a neutralizing step (i.e., a step that increases pH to about pH 7.0 to about pH 8.0) and a non-ionic detergent. Neither high pH alone nor non-ionic detergent alone produces such a protein extract. In particular embodiments, the high pH extraction reagent solubilizes proteins in the fixed cells, whereas the non-ionic detergent prevents the solubilized proteins in the intermediate composition from re-aggregating or precipitating as the pH of the intermediate composition is neutralized.

The reagents employed in the instant methods and the protein extract produced by the instant methods are described in greater detail below, as is a description of how the reagents may be used to produce the protein extract. As will be discussed below, the optimum concentration and pH of the reagents used in the instant methods may vary depending on which reagents are used. However, the optimum concentration and pH of the reagents are readily determined, either experimentally or empirically.

The Cells from which the Protein is Extracted by Using the Inventive Method

The methodology according to the present invention can be used to extract a target protein or protein of interest from a sample of cells. The sample of cells may be a homogenous population of cells, or a heterogenous mixture of cells of different type. The sample of cell may also contain "contaminants" such as mucous, blood cells and inflammatory cells which are not of interest for the purpose of extraction of the target protein or do not contain the target protein.

In some embodiments, the target protein is a viral protein present in cells infected with a virus, preferably a pathological virus, and the cells are preferably ones isolated from a mammal, e.g., a human.

The pathogenic virus may be any pathogenic virus that causes pathogenic effects or disease in human or other animals. The pathogenic virus may be various strains of human immunodeficiency virus (HIV), such as HIV-1 and HIV-2. The viral protein may be an HIV glycoprotein (or surface antigen) such as HIV GP120 and GP41, or a capsid protein (or structural protein) such as HIV P24 protein.

The pathogenic virus may be Ebola or Marburg virus. The viral protein may be an Ebola glycoprotein or surface antigen such as Ebola GP1 or GP2 protein.

The pathogenic virus may be hepatitis virus such as hepatitis A, B, C, D or E virus. For example, the viral protein may be a surface antigen or core protein of hepatitis B virus such as the small hepatitis B surface antigen (SHBsAg) (also referred to as the Australia antigen), the middle hepatitis B surface antigen (MHBsAg) and the large hepatitis B surface antigen (LHBsAg). The viral antigen may be a surface antigen or core protein of hepatitis C virus such as NS3, NS4 and NS5 antigens.

The pathogenic virus may be a respiratory syncytial virus (RSV). For example, the RSV viral protein may be the glycoprotein (G-protein) or the fusion protein (F-protein) of RSV.

The pathogenic virus may be a herpes simplex virus (HSV) such as HSV-1 and HSV-2. For example, the HSV viral antigen may be the glycoprotein D from HSV-2.

The target protein may be a tumor antigen, such as Her 2 of breast cancer cells and CD20 on lymphoma cells, a viral oncogene such as E6 and E7 of human papilloma virus, or a cellular oncogene such as mutated ras.

In some embodiments, the sample of cells contain fixed cells in which the target protein is present. The fixed cells employed in the instant methods are generally obtained by depositing a sample of cells (obtained by removing cells from a subject by dissection, exfoliation or lavage, for example) into a liquid medium. The sample of cells may be deposited into a liquid medium that already contains a chemical fixative, or a chemical fixative may be added to the liquid medium after the cells have been placed in the medium. A liquid medium containing a fixative and fixed cells is termed a "cellular sample" herein.

Representative chemical fixatives that may be employed in the instant methods include: alcohols (e.g., methanol or ethanol), aldehydes (e.g., gluteraldehyde or formaldehyde) and ketones (e.g., acetone), as well as osmium tetroxide, acetic acid, picric acid and heavy metal ion salts. Further examples of fixatives that may be employed in the instant methods include bi-sulfite-based fixatives (that may also include acetic acid), PVP-based fixatives (that may also contain propylene glycol and methanol) as well as those described in U.S. Pat. Nos. 3,546,334, 4,578,282, 4,857,300, 5,104,640, 5,256,571, 5,432,056 and 5,196,182. Examples of fixatives that may be employed in the instant methods, including the working concentrations of those fixatives, may be found in Baker, (Principles of Biological Microtechnique: A Study of Fixation and Dyeing, 1959) and Williams ("Tissue preparation for immunocytochemistry." J Clin. Pathol. 1997 50:422).

Of particular interest in the instant methods are liquid media that are termed "transport media" and routinely used for the collection, preservation (i.e., fixation) and transport of cervicovaginal cells (e.g., exfoliated cervical cells) as part of a gynecological examination. FDA approved transport media are of particular interest.

Examples of commercially available transport media that may be employed include: methanol-based PRESERV-CYT™ transport medium (which is sold as part of the THINPREP™ gynecological sampling kit of Cytyc, Inc., Marlborough, Mass.), ethanol-based SUREPATH™ transport medium formally known as CYTORICH™ (TriPath, Inc. Burlington, N.C.), and methanol-based CYTOLYT™ transport medium (Cytyc, Inc., Marlborough, Mass.) for example.

Cells may be obtained by any convenient method, including but not limited to exfoliation (e.g., scraping), dissection and lavage. Of particular interest are epithelial cells of cervical origin, which cells are typically obtained by exfoliating methods using an adapted brush, spatula or scraper, and deposited into a liquid medium containing fixative.

Extraction Reagent

The extraction reagent employed in the instant methods contains components that are present in amounts sufficient in concentration to produce a protein extract having a pH that is at least pH 10.0, upon addition of the extraction reagent to fixed cells. Accordingly, the extraction reagent generally has a pH of at least about pH 10.0.

The extraction reagent is contacted with the fixed cells to produce the intermediate composition. The pH of the extraction reagent and resulting intermediate composition is generally at least about pH 10.0, e.g., in the range of about pH 10.0 to about pH 13.0 or about pH 11.0 to about pH 12.0. In certain embodiments, the extraction reagent may have a pH of about pH 10.0 to about pH 10.5, pH 10.5 to about pH 11.0, pH 11.0 to about pH 11.5, pH 11.5 to about pH 12.0, pH 12.0 to about pH 12.5 or pH 12.5 to about pH 13.0. Extraction reagent may be made using any suitable source of hydroxide ions, e.g., sodium or potassium hydroxide or calcium carbonate, for example.

In certain embodiments, the extraction reagent may contain no significant amount of denaturant. However, in other embodiments, in addition to having a pH of at least 10.0, the extraction reagent may also contain a denaturant, e.g., an ionic detergent such as sodium dodecyl sulphate (SDS) or sarcosyl, or a chaotrophic agent such as urea. In these embodiments, the denaturant, if present, may be present at a concentration that does not significantly decrease the sensitivity of future assays. The concentration of denaturant may, in certain embodiments, be decreased during sample processing, e.g., by diluting the denaturant using neutralization buffer or by addition of a diluent, e.g., buffer or water to the protein extract prior to use.

Depending on strength of the denaturant used and the pH of the extraction buffer, the denaturant may be present in the extraction buffer at a concentration of about 0.01 M to about 0.05 M, about 0.05M to about 0.1 M, 0.1 M to about 0.2 M, about 0.2 M to about 0.5 M, about 0.5 M to about 1.0 M, about 1.0 M to about 2.0 M, about 2.0 M to about 4.0 M, or about 4.0 M to about 8.0 M. Denaturant, if present in the extraction reagent, may be present at a concentration that is well below the concentration of denaturant typically employed to denature protein. In other words, the extraction reagent may contain denaturant at a concentration that allows detection of a protein using a capture agent for that protein, after producing a protein extract according to the subject methods. The concentration of denaturant employed is generally sufficient to produce a protein extract containing proteins that are readily detectable in a binding assay that employs a capture agent, e.g., in an antibody detection assay.

Exemplary denaturants and their concentrations in a subject extraction reagent: sodium dodecyl sulphate (SDS): about 0.01% to about 2%, e.g., 0.05%, sarkosyl: about 0.01% to about 5%, e.g., 0.5%, guanidine: about 0.1 M to about 6 M, e.g., about 0.5M and urea: about 0.1 M to about 8 M, e.g., about 0.5 M, weight/vol.

SDS is typically employed to denature proteins at a concentration of 0.1% to 0.5%, sarkosyl is typically employed to denature proteins at a concentration of 2% w/v, urea is typically employed to denature proteins at a concentration of 2 M to 8 M, guanidine hydrochloride is typically employed to denature proteins at a concentration of 3 M to 8 M, N-cetyl trimethylammonium chloride is typically employed to denature proteins at a concentration of 5% w/v, and N-octylglucoside is typically employed to denature proteins at a concentration of 2%, w/v (See Protein purification Handbook, Amersham Pharmacia Biotech, p. 71 (1999)).

If no denaturant is present in an extraction reagent, the reagent may have a pH of at least about pH 11.0. If the extraction reagent contains detergent, then the pH of the extraction reagent may have a pH of at least about pH 10.0.

As will be described in greater detail below, the extraction reagent may, in certain embodiments, also contain a non-ionic detergent.

In certain embodiments, the extraction reagent may contain a buffer to maintain the reagent at a desired pH. If a buffer is present in a subject extraction reagent, the buffer may have a $pk_\alpha$ in the range of about 9.0 to about 12.5 at 25° C. Exemplary buffers that may be employed in a subject protein extraction reagent include CABS, piperidine, phosphate, CAPS, glycine or ethanolamine, for example. Buffers that have little or no buffering capacity at a pH of above about pH 10.0 (e.g., tris, tricine, hepes, etc.) are generally not employed to buffer the pH of the extraction reagent, but may nevertheless be present in an extraction reagent.

The subject protein extract reagent may contain other components e.g., salt ion chelators, protease inhibitors, etc., in addition to the above-recited components.

The protein extraction reagent may be a liquid or solid composition and may, in certain embodiments, contain a combination of different denaturants.

Denaturants that may be employed in the instant extraction buffer are generally strong denaturants and include but are not limited to: chaotrophic agents (e.g., urea, guanidine hydrochloride, or a thiocyanate salt such as sodium thiocyanate or guanidinium thiocyanate, sodium iodide, sodium perchlorate and the like; see K. Hamaguchi et al., Proc. Natl. Acad. Sci. 62: 1129-1136, 1962) and ionic detergents (e.g., sodium dodecyl sulfate (SDS), sarcosyl or N-cetyl trimethylammonium chloride), including cationic, anionic and zwitterionic detergents (such as CHAPS or CHAPSO). Further denaturants that may be employed in the instant methods are listed in columns 7 and 8 of U.S. Pat. No. 6,488,671, which patent is incorporated herein by reference in its entirety.

In certain embodiments, a weak denaturant such as LiCl, $LiClO_4$, LiBr, $CaCl_2$ or NaCl is not employed as a denaturant in the extraction buffer, although such a compound may be present in a extraction buffer or protein extract in addition to a denaturant listed in the previous paragraph.

As noted above, the extraction reagent is contacted with (e.g., combined or mixed with) fixed cells. In certain embodiments, a cellular sample containing the fixed cells (e.g., a transport medium containing fixed cells) may be directly added to the extraction reagent. In other embodiments, the fixed cells may be isolated from the cellular sample (e.g., by sedimentation, centrifugation, filtration or affinity methods), prior to their addition to the protein extraction reagent. Cells may be washed or contacted with other reagents prior to their addition to the extraction reagent.

All or a portion of the available fixed cells may be combined with the extraction reagent. For example, in certain embodiments, a portion of the fixed cells may be employed in cytology test and a portion of the fixed cells may be contacted with the extraction reagent to produce the intermediate composition. The fixed cells and extraction reagent may be combined and maintained under suitable temperature (e.g., on ice, at about room temperature or at about 37° C.) and for a suitable time (e.g., from 10 seconds to 24 hr) to produce the intermediate composition. In certain embodiments, the neutralizing reagent is contacted with the intermediate composition immediately after the fixed cells have been contacted with the extraction reagent.

Neutralizing Reagent

The neutralizing reagent employed in the instant methods has a pH that is sufficient to neutralize the pH of the intermediate composition discussed above, upon contact with the intermediate composition. In other words, the neutralizing reagent contains a non-ionic detergent and has a pH that is sufficient to neutralize the pH of the intermediate composition discussed above when the neutralizing reagent is mixed with the intermediate composition. As will be described in greater detail below, the neutralizing reagent may, in certain embodiments, contain a non-ionic detergent.

The pH of the neutralizing reagent is sufficient to neutralize the intermediate composition made by contacting fixed cells with a subject extraction reagent. Depending upon the pH of the extraction reagent and whether buffers are employed, the pH of the neutralizing reagent may be between pH 4.0 to pH 8.0. In certain embodiments, the neutralizing reagent may have a pH of about pH 4.0 to about pH 4.5, pH 4.5 to about pH 5.0, pH 5.0 to about pH 5.5, pH 5.5 to about pH 6.0, pH 6.0 to about pH 6.5, pH 6.5 to about pH 7.0 or pH 7.0 to about pH 7.5. Neutralizing reagent may be made using any suitable source of hydrogen ions, e.g., hydrochloric acid or acetic acid, for example. In certain embodiments, the neutralizing reagent may have a pH of less than pH 4.0.

The neutralizing reagent may be buffered or not buffered. If the neutralizing reagent is buffered, then the neutralizing reagent may be buffered using any buffer having a $pK_a$ of about 6 to about 8, e.g., tris, hepes or tricine, for example.

As noted above, either the extraction reagent and/or the neutralizing reagent may contain a non-ionic detergent.

In certain embodiments, the non-ionic detergent employed may be nonidet P-40, n-octylglucoside, a TRITON™ detergent such as TRITON™ X-100, octyl β-thioglucopyranoside, a TWEEN™ detergent such as TWEEN-20, or NP-40). Depending on strength of the detergent used, the detergent may be present in the extraction buffer or the neutralizing buffer at a concentration of about 0.01 M to about 0.05 M, about 0.05M to about 0.1 M, 0.1 M to about 0.2 M, about 0.2 M to about 0.5 M, about 0.5 M to about 1.0 M, about 1.0 M to about 2.0 M, about 2.0 M to about 4.0 M, or about 4.0 M to about 8.0 M. Further detergents that may be employed in the instant methods are listed in columns 7 and 8 of U.S. Pat. No. 6,488,671, which patent is incorporated herein by reference in its entirety. In certain embodiments, the detergent may be present in both the extraction and the neutralizing buffer.

Exemplary detergents and their concentrations in a subject neutralizing and/or extraction reagent include: Triton X-100: about 0.1% to about 10%, e.g., about 1%, NP40: about 0.1% to about 10%, e.g., about 1% and Tween-20: about 0.1% to about 10%, e.g., about 1%, weight/vol.

As noted above, the neutralizing reagent is contacted with (e.g., combined or mixed with) the intermediate composition to produce a protein extract having a neutral pH (i.e., a pH in the range of about pH 6.5 to about pH 8.0, e.g., in the range of about pH 7.0 and about pH 7.8). The protein extract further contains protein from fixed cells, a non-ionic detergent at a concentration listed above, and in certain embodiments, a buffer for maintaining the protein extract in a particular pH range. If a denaturant is added to the fixed cells, the protein extract may further contain that denaturant. The pH, choice of detergent and concentration of the detergent employed (and, if a denaturant is employed, the identity and concentration of the denaturant) are sufficient to allow the protein extract to be directly employed in a binding assay to detect proteins present in the protein extract.

Neutralization of the cell extract may also be carried out by passing the extract through a filter or filter tip that is impregnated with neutralizing reagent. As the extract passes through the filter material, neutralizing reagent is solubilized and the pH of the extract approaches neutrality.

An alternative method for neutralizing the cell extract is to pass the extract through a BioSpin column (BioRad) pre-equilibrated with a solution at neutral pH. The extract may also be placed in a syringe or similar apparatus that contains gel (or filtering material) containing neutralizer and delivered from the syringe by positive pressure.

In certain embodiments, the subject protein extract contain solubilized HPV E6 protein (particularly E6 protein from oncogenic strains of HPV) that is accessible to and readily detectable by a capture agent without further treatment of the protein extract (e.g., without further addition of denaturant, pH changes or heating). The protein extract may also contain solubilized or insoluble membranes, proteins other than HPV E6 protein, and other cellular contents such as DNA, RNA, carbohydrates, etc. Other contaminants such as those derived from mucal contamination of the original cellular sample may also be present. The components of the protein extract generally do not contain whole (i.e., cytologically intact) cells.

The protein extract may be used immediately, or stored, e.g., in frozen form, before use.

In particular embodiments, the protein extracts produced by the methods set forth above may be employed in protein detection methods, which methods are described in greater detail below.

As would be apparent from the above, a variety of different denaturants, detergents, buffers, pHs and component concentrations may be employed in the reagents described above. The optimal denaturant, detergent, buffer or pH, or component concentration in any reagent is readily determined using routine methods.

After neutralization of the cell extract, E6 protein may be concentrated from the cell extract by incubating the extract with particles containing binder for the E6. The binder may comprise PDZ, E6 Associated Protein (E6AP) or fragments thereof, or E6 Binding Protein (E6BP) or fragments thereof. After E6 is captured by the particles, the particles are washed and E6 is then released from the particles by incubation with buffer at pH greater than 10. The particles are separated from the eluting solution and the remaining solution is then neutralized by the procedures described previously. Alternatively, E6 protein may be detected without release form the capture particles.

Protein Detection Methods

The protein extract made by the methods discussed above may be employed directly or indirectly (i.e., after addition of further reagents) in a methods in which the presence of one or more proteins in the protein extract is assessed. The protein detection methods generally involve a capture agent that specifically binds to a protein. The identity of the proteins to be detected may be of known (i.e., pre-determined) or unknown identity at time of performing the method.

Proteins that may be detected using the subject protein detection methods include proteins that are diagnostic markers a disease or condition, e.g., cancer, inflammatory disease, or infection by virus, bacteria or fungus, for example. In certain embodiments, a protein detected using the subject methods is not routinely detectable unless the subject protein extraction methods are employed.

Exemplary proteins that may be detected using the instant methods include proteins that are encoded by an infectious agent, such as human papilloma virus (HPV). In particular embodiments, the instant methods may be employed to detect the E6 protein of HPV, a protein that has proven difficult or impossible to detect in protein extracts made from fixed cells by other methods.

In general terms, protein detection methods are very well known in the art and include binding assays, i.e., assays in which binding between a protein and a capture agent for the protein are detected. Such assays include immunoassays, i.e., binding assays that employ an antibody that specifically binds to a protein, including, but not limited to, competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, and protein A immunoassays, to name but a few. Such assays are routine and well known in the art (see, e.g., Ausubel et al, eds, 1994, Current Protocols in Molecular Biology, Vol. 1, John Wiley & Sons, Inc., New York, which is incorporated by reference herein in its entirety). Exemplary immunoassays are described briefly below.

Immunoprecipitation protocols generally involve producing a protein extract, adding a capture agent, e.g., an antibody, to the protein extract and incubating the protein extract and capture agent for a suitable period of time and temperature. The capture agent is then bound to a solid support, e.g., an affinity substrate such as beads linked to protein A and/or protein G, and the mixture is incubated and washed. The solid support is resuspended in sample buffer and the protein of interest may be detected by western blotting, for example.

ELISAs may involve preparing a protein extract, linking the protein extract to a solid support (e.g., a well of a multi-well microtiter plate), contacting the support-bound protein extract with a capture agent, e.g., an antibody, and detecting binding between the capture agent and the protein. In certain ELISA methods, the capture agent may be detectably labeled with a detectable moiety such as an enzymatic substrate (e.g., horseradish peroxidase or alkaline phosphatase) prior to contacting the capture agent with the support-bound protein extract. In other embodiments, however, binding of the capture agent to the protein extract may be detected by a detectably second capture agent (e.g., a second antibody) that binds to the capture agent contacted with the protein extract.

In other ELISA assays, the capture agent may be finked to a solid support, and the protein extract is contacted with the solid support-bound capture agent. Binding of a protein in the protein extract to the solid-support antibody may be detected using a second capture agent for the protein. Such "sandwich assays" are well known in the art.

In other assays, binding between a capture agent and the protein may occur in solution prior to surface immobilization of the capture agent.

In particular, the instant methods may be employed to detect the E6 protein from oncogenic strains of HPV. In these embodiments, the capture agent employed in the detection method may be, for example, an antibody or a polypeptide comprising a PDZ domain that binds to a PDZ ligand (i.e., a binding site for a PDZ domain) contained in the E6 protein. For example, the instant E6 detection binding method may employ a PDZ domain-containing protein that contains the second PDZ of MAGI-1, or the PDZ domain of DLG or TIP1, etc, as described in published application US 20040018487 (published on Jan. 29, 2004) and incorporated herein by reference in its entirety. Exemplary PDZ domain-containing proteins and PDZ domain sequences are shown in TABLE 2 and EXAMPLE 4 of application US 20040018487. The term "PDZ domain" also encompasses variants (e.g., naturally occurring variants) of the sequences (e.g., polymorphic variants, variants with conservative substitutions, and the like) and domains from alternative species (e.g. mouse, rat). Typically, PDZ domains are substantially identical to those shown in U.S. patent application Ser. No. 09/724,553 which is herein incorporated by reference, e.g., at least about 70%, at least about 80%, or at least about 90% amino acid residue identity when compared and aligned for maximum correspondence. It is appreciated in the art that PDZ domains can be mutated to give amino acid changes that can strengthen or weaken binding and to alter specificity, yet they remain PDZ domains (Schneider et al., 1998, Nat. Biotech. 17:170-5). Unless otherwise indicated, a reference to a particular PDZ domain (e.g. a MAGI-1 domain 2) is intended to encompass the particular PDZ domain and HPV E6-binding variants thereof. In other words, if a reference is made to a particular PDZ domain, a reference is also made to variants of that PDZ domain that bind oncogenic E6 protein of HPV, as described below. In this respect it is noted that the numbering of PDZ domains in a protein may change. For example, the MAGI-1 domain 2 (of amino acid sequence PSELKGKFIHTKLRKSSRGFGFTVVG-GDEPDEFLQIKSLVL DGPAALDGKMETGDVI VSVNDTCVLGHTHAQWKIFQSIPIGASVDLELCRGY-PLPFDPDDPN), as referenced herein, may be referenced as MAGI-1 domain 1 in other literature. As such, when a particular PDZ domain of a protein is referenced in this application, this reference should be understood in view of the sequence of that domain, as described herein, particularly in the sequence listing Table 2 of Application US 20040018487, shows the relationship between the sequences of the sequence listing and the names and Genbank accession numbers for various domains; where appropriate. As used herein, the term "PDZ protein" refers to a naturally occurring protein containing a PDZ domain. Exemplary PDZ proteins include CASK, MPP1, DLG1, DLG2, PSD95, NeDLG, TIP-33, SYN1a, TIP-43, LDP, LIM, LIMK1, LIMK2, MPP2, NOS1, AF6, PTN-4, prIL16, 41.8 kD, KIAA0559, RGS12, KIAA0316, DVL1, TIP-40, TIAM1, MINT1, MAGI-1, MAGI-2, MAGI-3, KIAA0303, CBP, MINT3, TIP-2, KIAA0561, and TIP-1. As used herein, the term "PDZ-domain polypeptide" refers to a polypeptide containing a PDZ domain, such as a fusion protein including a PDZ domain sequence, a naturally occurring PDZ protein, or an isolated PDZ domain peptide. A PDZ-domain polypeptide may therefore be about 60 amino acids or more in length, about 70 amino acids or more in length, about 80 amino acids or more in length, about 90 amino acids or more in length, about 100 amino acids or more in length, about 200 amino acids or more in length, about 300 amino acids or more in length, about 500 amino acids or more in length, about 800 amino acids or more in length, about 1000 amino acids or more in length, usually up to about 2000 amino acids or more in length, about 50-2000 amino acids in length, about 50-1500 amino acids in length, about 50-1000 amino acids in length, about 60-1000 amino acids in length, about 70-1000 amino acids in length. PDZ domain peptides are usually no more than about 200 amino acids (e.g. 50-200 amino acids, 60-180 amino acids, 80-120 amino acids, or 90-110 amino acids), and encode a PDZ domain.

Antibodies suitable for detecting the E6 protein of HPV are described in 20050142541 (published on Jun. 30, 2005), for example. Detailed methods for identifying the E6 protein from oncogenic strains of HPV are found in published U.S. patent application US20040018487, which methods are incorporated herein in their entirety. These published methods are readily adapted for employment in the instant methods.

In certain embodiments, an anti-E6 antibody may be bound to a solid support, and a protein extract produced by the subject methods is contacted with the solid support bound antibody. Binding of oncogenic E6 protein in the protein extract may be detected using a PDZ domain-containing protein. In other embodiments, a PDZ domain-containing protein may be bound to a solid support, and a protein extract produced by the subject methods is contacted with the solid support bound PDZ domain-containing protein. Binding of oncogenic E6 protein in the protein extract may be detected using an anti-E6 antibody. In alternative methods, binding between the antibody of PDZ domain-containing protein may occur in solution (i.e., in the absence of binding of either the antibody or PDZ domain-containing protein to a solid support), and, after binding, the antibody or PDZ domain-containing protein may be bound a solid support (e.g., beads or the like). In these embodiments, the PDZ domain-containing protein may be a fusion protein having an affinity domain that binds to the solid support. The presence of the E6 protein can be detected using a second capture agent that recognizes the E6 protein.

Results obtained from the assay methods described above may be compared to results obtained from suitable controls, e.g., a positive control (in which a protein extract known to contain the protein to which the capture agent binds may be employed) or a negative control (e.g., in which a protein extraction reagent that has not been contacted with a cellular sample may be employed).

Results obtained from the assay methods described above may indicate the presence, absence, or, in certain embodiments, the amount of a protein in a protein extract.

In certain embodiments, the results obtained from the assay methods described above may be communicated back to a remote location, e.g., by telephone, fax, e-mail, mail or any other means. The results may be communicated to the subject or a subject's doctor, for example.

The above protein detection methods may be performed in combination with a different test, such as a cytological test, e.g., a Pap test for identifying cancerous or pre-cancerous cervical cells, or other molecular tests. In these embodiments, the cellular sample may be divided into parts prior to use. The first part may be used in cytological assays and the second part may be used in the above-described methods.

In accordance with the above, certain embodiments of the invention also provide a system for producing a protein extract. The system generally contains: a) a cellular sample containing fixed cells; b) an extraction reagent that has a pH of at least about pH 10.0; and c) a neutralizing reagent, where the fixed cells, extraction reagent and neutralizing agent may be employed in the above methods to produce a protein extract suitable for use in a binding assay. The extraction reagent and/or the neutralization reagent contains a non-ionic detergent.

Kits

In yet another aspect, the present invention provides kits for practicing the subject methods, e.g., for producing a protein extract from a fixed cells, in certain embodiments, for testing for the presence of a protein in the protein extract. The subject kits at least include an extraction reagent that has a pH of at least about pH 10.0, and a neutralizing reagent. The extraction reagent and/or the neutralizing reagent contains a non-ionic detergent. In addition, the kits may include a capture agent for detecting a protein, and, in certain embodiments, reagents (e.g., buffers and detection reagents) for detecting that protein using the capture agent. The above components may be present in separate containers or one or more components may be combined into a single container, e.g., a glass or plastic vial.

In addition to the above components, the subject kits may further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, etc., on which the information has been recorded. Yet another means that may be present is a website address which may be used via the internet to access the information at a removed site. Any convenient means may be present in the kits.

Utility

The method and system described above are readily employed in a variety of research and diagnostic methods, including methods of diagnosing a particular disease or condition, or infection by an infections agent, such as a virus or bacteria. In one embodiment, the method is employed as part of a diagnostic for detecting HPV infected cells. Since the presence of oncogenic strains of HPV is associated with cancerous and pre-cancerous cells, the instant methods may be employed to detect cancerous or pre-cancerous cervical cells.

HPV is known to be a causative agent in the following diseases: epidermodysplasia verruciformis (EV), a lifelong skin disorder that results in high risk for skin (e.g., squamocelllar) cancer; cervical neoplasias such as cervical intraepithelial neoplasia (CIN) and invasive cervical carcinoma (ICC); viginal neoplasias such as vaginal intraepithelial neoplasia (VAIN) and vaginal carcinoma (VC); vulval neoplasias such as vulvar intraepithelial neoplasia (VIN) and vulvar carcinoma; penile carcinoma (including Bowenoid papulosis); anal (AC) and perianal carcinomas (PC); oropharyngeal carcinomas (OS); esophageal carcinomas (EC); non-melanoma skin cancers (e.g., basal cell carcinoma-BCC and squamous cell carcinoma-SCC); and melanoma. As such, in one embodiment, the instant methods may be employed as a diagnostic for any of these diseases.

In one embodiment, cells are obtained (e.g., exfoliated or dissected) from a subject and deposited into a liquid medium containing a fixative that, in certain embodiments, may be a transport medium for cytological test. The cells are usually obtained in doctor's office or clinic, the cellular sample is forwarded to and received by a testing facility in which the above-recited protein detection methods and, optionally, cytology assays are performed. Results from the testing are communicated to the subject, in some embodiments via the doctor and an associate thereof.

The subject from which cells are employed may be a mammal, e.g., a dog or cat, a rodent (e.g., mouse, guinea pig, or rat), or primate (e.g., a human, chimpanzee, or monkey). In many embodiments, the subject will be a human, particularly a male or female. In certain embodiments, the subject may show symptoms of HPV infection (e.g., may have warts on one or more parts of the body), may be suspected of being infected by HPV (e.g., may contain cells that are cytologically consistent with such an infection) or may have already tested positive for HPV. In certain embodiments, the subject may have no indication of HPV infection, and the above methods may be employed as part of a routine screen.

In one embodiment, the instant methods may be employed to detect any strain of oncogenic HPV, e.g., HPV 26, HPV 53, HPV 66, HPV 73, HPV 82, HPV 16, HPV 18, HPV 31, HPV 35, HPV 30, HPV 39, HPV 45, HPV 51, HPV 52, HPV 56, HPV 59, HPV 58, HPV 33, HPV 66, HPV 68 or HPV 69, (particularly any of the most prevalent HPV strains, e.g., HPV 16, HPV 18, HPV 31, HPV 33 and HPV 45) by detecting the E6 protein from that strain. In one embodiment, at the point of initiating the instant methods, it is not known if the fixed cells contain oncogenic E6 protein or which strain an oncogenic E6 protein is from. If a detection assay indicates the presence of an oncogenic E6 protein in fixed cells, then the identity of the strain of HPV that infected those cells can be determined by other molecular assays, e.g., those that employ antibodies specific to a particular E6 protein or other protein encoded by the virus, or by sequencing viral DNA.

The following examples are offered by way of illustration and not by way of limitation.

EXPERIMENTAL

Extraction of Spiked Clinical Samples

Cells transfected with the HPV16E6 gene (C33A+) were fixed with THINPREP™ medium and added (i.e., "spiked") into portions of the THINPREP™-fixed clinical samples as listed below. The cells were spiked into half of each of five clinical samples (each half clinical sample having 20 million C33A+ cells).

Extraction Scheme:
C33A(+) ThinPrep cells/20M cells per ml
1—20M C33A(+) ThinPrep cells into ½ clinical negative #229 (1.0 ml extraction)
2—20M C33A(+) ThinPrep cells into ½ clinical negative #230 (1.0 ml extraction)
3—20M C33A(+) ThinPrep cells into ½ clinical negative #231 (1.0 ml extraction)
4—20M C33A(+) ThinPrep cells into ½ clinical negative #232 (1.0 ml extraction)
5—20M C33A(+) ThinPrep cells into ½ clinical negative #233 (1.0 ml extraction)
6—20M C33A(+) ThinPrep cells (1.0 ml extraction)

Extraction Reagent:
Triton X-100/Lot 092K0171—(1%=250 ul)
5M NaCl/Lot 5701-53—(0.15M=750 ul)
0.5M Tris Base/Lot 5708-20—(0.1M=5 ml)
0.5M Glycine/Lot 5708-9—(0.1M=5 ml)
10% SDS/Lot 5708-8—(0.05%=125 ul)
8M Urea/Lot 5678-83—(0.25M=781 ul)
Add RO/DI to 20 ml—(8.1 ml)
5N NaOH/Lot A09522—(525 ul)
Add RO/DI to 25 ml—(4.475 ml)
Final pH—11.48

Final formulation: 0.1 M Tris/0.1 M glycine/0.15 M NaCl/1% Triton X-100/0.05% SDS/0.25 M urea pH 11.48

Protein Extraction Procedure:

1. Add cell suspension to 50 ml centrifuge tube
2. Spin at 3000 rpm for 10-15 minutes
3. Carefully remove supernatant
4. Transfer contents to a 1.5 ml nunc tube
5. Spin at 3000 rpm for 10-15 minutes
6. Carefully remove supernatant
7. Add required quantity of extraction reagent to pellet
8. Re-suspend to break up cell pellet
   a. Additives (DTT @ 1:100)
9. Check pH, adjust to 11.5
10. Mix at RT (or appropriate temperature for extraction) for 30 minutes
11. Spin at 14,000 rpm for 10-15 minutes
12. Remove clarified supernatant
13. Add DTT @ 1:100
14. Neutralize to pH 8.0 with 5N HCl and test in ELISA (Neutralize to pH 8.0 with 31.0 ul 5N HCl/1 ml) 100 mM DTT/NR 5701-90/DOM 2/7/05

ELISA Method

1—Coat plate (Nunc 439454 Maxisorp F96/lot 542043) with 5 ug/ml GST-Magi-PDZ (lot 88.18/0.65 ug/ul) in PBS (lot 021405)—100 ul per well 11 ml×5 ug/ml=55 ug×1 ul/0.65 ug=84.6 ul GST-Magi-PDZ 2—Incubate overnight at 4° C.
3—Wash 3× (TBS-Tween) with plate washer
4—Block plate with 250 ul blocking buffer (lot 033005)
5—Incubate for 2 hours 25° C.
6—Wash 3× (TBS-Tween) with plate washer
7—Add 100 ul MBP-E6/lysate sample to appropriate wells
8—Incubate for 1 hour 25° C.
9—Wash 3× (TBS-Tween) with plate washer
10—Add 100 ul of anti-E6 antibody (4C6–2.85 mg/ml—lot 02) @ 5 ug/ml to appropriate well in 2% BSA HNTG buffer (lot 031805B). N-terminus peptide (HPV16E6 lot#PN3952-2) is added to appropriate samples at 10 ug/ml to verify signal specificity (peptide is pre-incubated with the anti-E6 antibody for 45 minutes prior to addition).
11—Incubate for 2 hour 25° C.
12—Wash 3× (TBS-Tween) with plate washer
13—Prepare a 1:5000 dilution of goat anti-mouse IgG-HRP (Jackson G×M IgG-HRP/catalog #115-035-062/lot 60988) in 2% BSA/0.05% Tween 20 buffer (lot 040505).

10.0 ml×1/5000=0.002 ml×1000 ul/ml=2.0 ul goat anti-mouse IgG-HRP

14—Add 100 ul 1:5000 goat anti-mouse IgG-HRP dilution to appropriate wells
(Remove TMB Substrate and place at room temperature)
15—Incubate for 1 hour 25° C.
16—Wash 5× (TBS-Tween) with plate washer
17—Add 100 ul Neogen K-Blue TMB Substrate (lot 041018)
18—Incubate for 30 minutes at 25° C.
19—Add 100 ul Stop Solution (lot 030705) and Read A450

Formulation:

2% BSA/0.05% Tween buffer—(lot 040505)

2% BSA blocker lot 033005 (49.975 ml)

Tween 20 lot A016759301 (0.025 ml)

RESULTS

| | Sequential (NO peptide) | | | Sequential (N-terminus peptide) | | |
|---|---|---|---|---|---|---|
| | OD | | Average | Average | OD | |
| 20M C33A(+) TP cells in ½ clinical negative #229* | 1.294 | 1.220 | 1.257 | 0.464 | 0.516 | 0.411 |
| 20M C33A(+) TP cells in ½ clinical negative #230* | 1.140 | 1.103 | 1.122 | 0.631 | 0.630 | 0.632 |
| 20M C33A(+) TP cells in ½ clinical negative #231* | 1.136 | 1.178 | 1.157 | 0.443 | 0.451 | 0.434 |
| 20M C33A(+) TP cells in ½ clinical negative #232* | 0.946 | 0.924 | 0.935 | 0.580 | 0.585 | 0.574 |
| 20M C33A(+) TP cells in ½ clinical negative #233* | 1.288 | 1.169 | 1.229 | 0.843 | 0.843 | 0.843 |
| 20M C33A(+) TP cells | 1.762 | 1.691 | 1.727 | 0.345 | 0.334 | 0.356 |
| C33A(+)/2M cells/LB (+ve) | 2.052 | 2.134 | 2.093 | | | |
| C33A(−)/2M cells/LB(−ve) | 0.167 | 0.188 | 0.178 | | | |
| Anti-4C6 + N-Term (−ve) | 0.056 | 0.062 | 0.059 | | | |
| Anti-4C6 (−ve) | 0.106 | 0.115 | 0.111 | | | |

*Extraction volume - 1 ml

As can been seen from the results shown in the above table, E6 binding was detected for all spiked clinical samples.

It is evident that from the above results and discussion that the subject methods provide a number of distinct advantages for the molecular analysis of fixed cells. In particular, the methods provides a routine method for the production of a protein extract from fixed cells in which proteins in the protein extract are detectable in binding assays. Since it is generally difficult to detect certain proteins in fixed cells, the subject invention represents a significant contribution to the art.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A method for producing a protein extract from human epithelial cells in which a human papillomavirus (HPV) protein is present, comprising:
   a) contacting said human epithelial cells in which said HPV protein is present with an extraction reagent, thereby producing an intermediate composition comprising said HPV protein and having a pH of greater than pH 10.0; and
   b) contacting said intermediate composition comprising said HPV protein with a neutralizing reagent that comprises a source of hydrogen ions, thereby neutralizing said pH of said intermediate composition and also thereby producing said protein extract, wherein said protein extract comprises said HPV protein;
   wherein said extraction reagent or said neutralizing reagent comprises a non-ionic detergent.

2. The method of claim 1, wherein said HPV protein is an E6 or E7 protein.

3. The method of claim 1, wherein said HPV protein is an E6 protein.

4. The method of claim 1, wherein said HPV protein is an E7 protein.

5. The method of claim 1, further comprising:
   receiving a cellular sample comprising said human epithelial cells prior to step a), wherein said human epithelial cells are from a subject with symptoms of HPV infection.

6. The method of claim 1, wherein said human epithelial cells are cervical cells.

7. The method of claim 1, wherein said human epithelial cells are present in an ethanol-based or methanol-based transport medium.

8. The method of claim 1, wherein said pH in step a) is in a range of pH 11.0 to pH 13.

9. The method of claim 1, wherein said non-ionic detergent is octylphenolpoly(ethyleneglycolether)$_x$ or a polysorbate detergent.

10. The method of claim 1, wherein said human epithelial cells are exfoliated cervical cells.

11. The method of claim 1, wherein said HPV protein is from an HPV strain selected from the group consisting of HPV 4, HPV 11, HPV 20, HPV 24, HPV 28, HPV 36, HPV 48, HPV 50, HPV 16, HPV 18, HPV 31, HPV 35, HPV 30, HPV 39, HPV 45, HPV 51, HPV 52, HPV 56, HPV 59, HPV 58, HPV 33, HPV 66, HPV 68, HPV 69, HPV 26, HPV 53, HPV 73, and HPV 82.

12. The method of claim 1, wherein said HPV protein is from an oncogenic HPV strain selected from the group consisting of HPV 26, HPV 53, HPV 66, HPV 73, HPV 82, HPV 16, HPV 18, HPV 31, HPV 35, HPV 30, HPV 39, HPV 45, HPV 51, HPV 52, HPV 56, HPV 59, HPV 58, HPV 33, HPV 66, HPV 68, HPV 69, and HPV 82.

13. The method of claim 1, wherein said human epithelial cells are from a cell sample that further contains mucous or blood.

14. The method of claim 1, wherein said human epithelial cells are fixed cells.

15. The method of claim 1, wherein said human epithelial cells are fixed with a chemical fixative.

16. The method of claim 1, wherein said human epithelial cells are fixed with a chemical fixative that is selected from the group consisting of alcohols, aldehydes, ketones, osmium tetroxide, acetic acid, picric acid, heavy metal ion salts, and propylene glycol.

17. The method of claim 1, wherein said neutralizing reagent comprises hydrochloric acid or acetic acid.

18. The method of claim 1, wherein said extraction reagent comprises said non-ionic detergent.

19. The method of claim 1, wherein said neutralizing reagent comprises said non-ionic detergent.

20. The method of claim 18, wherein said extraction reagent contains no denaturant or denaturant at a concentration lower than a concentration typically employed to denature proteins.

21. The method of claim 18, wherein concentration of denaturant in said extraction reagent is less than 0.1%.

22. The method of claim 1, wherein said HPV protein is from an oncogenic HPV strain selected from the group consisting of HPV 16, HPV 18, HPV 31, HPV 35, HPV 45, HPV 52, and HPV 58.

23. The method of claim 1, wherein both of said extraction reagent and said neutralizing reagent comprise a non-ionic detergent.

24. The method of claim 1, wherein said extraction reagent has a pH greater than pH 10.0.

25. The method of claim 1, wherein said extraction reagent comprises sodium or potassium hydroxide.

26. The method of claim 1, wherein said extraction reagent comprises calcium carbonate.

* * * * *